United States Patent
Nimkar et al.

(10) Patent No.: US 6,530,898 B1
(45) Date of Patent: Mar. 11, 2003

(54) VISUAL INFLATION PRESSURE INDICATOR AND SURGICAL TUBE INCLUDING THE INDICATOR

(75) Inventors: Shekhar D. Nimkar, Swampscott, MA (US); E. David Fink, Franklin, MA (US); David S. Sheridan, Argyle, NY (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 09/552,913

(22) Filed: Apr. 20, 2000

(51) Int. Cl.[7] ............................................. A61M 29/00
(52) U.S. Cl. ................. 604/97.03; 604/100.01
(58) Field of Search ...................... 604/100.01–100.03, 604/920, 97.01–97.03, 99.01–99.03; 600/561, 593; 128/207.12, 207.14–207.16; 607/98.01, 98.02

(56) References Cited

U.S. PATENT DOCUMENTS

| | | | |
|---|---|---|---|
| 2,473,742 A | 6/1949 | Auzin | |
| 3,192,949 A | 7/1965 | DeSee | |
| 3,407,817 A | 10/1968 | Galleher, Jr. | |
| 3,546,944 A | 12/1970 | Mack | |
| 3,625,199 A | 12/1971 | Summers | |
| 3,731,692 A | 5/1973 | Goodyear | |
| 3,831,629 A | 8/1974 | Mackal et al. | |
| 3,848,605 A | 11/1974 | Harautuneian et al. | |
| 4,016,885 A | 4/1977 | Bruner | |
| 4,018,231 A | 4/1977 | Wallace | |
| 4,134,407 A | 1/1979 | Elam | |
| 4,178,939 A | * 12/1979 | Stephens | 604/100.01 |
| 4,266,550 A | * 5/1981 | Bruner | 604/100.01 |
| 4,361,107 A | 11/1982 | Gereg | |
| 4,592,747 A | 6/1986 | Pool | |
| 4,617,015 A | 10/1986 | Foltz | |
| 4,681,132 A | 7/1987 | Lardner | |
| 4,776,369 A | 10/1988 | Lardner | |
| 4,856,510 A | * 8/1989 | Kowalewski | 604/99.04 |
| 5,487,731 A | 1/1996 | Denton | |
| 5,591,130 A | 1/1997 | Denton | |

* cited by examiner

*Primary Examiner*—Anhtuan T. Nguyen
(74) *Attorney, Agent, or Firm*—Burns, Doane, Swecker & Mathis, LLP

(57) ABSTRACT

The present invention provides an indicator for visually indicating a pressure level of a fluid in a pressure source. The indicator comprises an inflatable body having a notched section with opposing edge portions that are separated by a gap when the inflatable body is in an uninflated condition. The inflatable body further includes a port for connecting the inflatable body to the pressure source whereby upon inflation of the inflatable body, there is relative movement of the opposing edge portions in a direction so as to decrease the size of the gap and thereby indicate that a predetermined pressure has been reached in the pressure source. The indicator is particularly for indicating whether a predetermined pressure has been reached in an inflation cuff of an endotracheal tube.

21 Claims, 2 Drawing Sheets

VISUAL INFLATION PRESSURE INDICATOR AND SURGICAL TUBE INCLUDING THE INDICATOR

BACKGROUND OF THE INVENTION

A. Field of the Invention

The present invention relates to a visual pressure indicator. The present invention further relates to an endotracheal cuff including an inflatable visual pressure indicator.

B. Description of the Related Art

There are many situations when it is important to determine the level of the fluid pressure in a device. The situations can vary from liquid or gas flowing in a conduit to the air pressure in a tire or inflated device, such as an air mattress. One particularly important device in which it is necessary to determine fluid pressure is in an endotracheal tube.

An endotracheal tube is a medical device used in emergency and other situations to prevent blockage of a patient's airway and/or provide general anesthesia during a surgical procedure. Endotracheal tubes are used for allowing the passage of respiratory or anesthetic gases into the lungs, while preventing entry of secretions from the upper airway of a patient into the patient's trachea and lungs. The endotracheal tube also provides a passageway for a suction catheter to be inserted into the trachea to remove accumulation of mucus from the lung passageway and thereby to prevent infections.

An endotracheal tube comprises a flexible tube, usually made from plastic such as polyvinyl chloride ("PVC"), having an inflatable cuff at one of its ends. The tube is inserted into the trachea so that the cuff is inserted below the vocal cords and above the bronchial tubes of the patient. The cuff, once inflated, seals the tube against the walls of the trachea.

The cuff is inflated by way of a cuff inflation tube which is formed within the wall of the tube which connects the cuff to an air source. A valve is fitted to the end of the cuff inflation tube to accommodate the air source, typically a syringe. The syringe is used to inflate the cuff with air via the cuff inflation tube.

In order to obtain the benefits of using an endotracheal tube, the cuff must be properly inflated. However, because the cuff is enclosed by the walls of the trachea, a visual indication of proper inflation is not possible. In addition, there is a tendency to overinflate the cuff, thereby causing damage to the walls of the trachea. Moreover, even if originally properly inflated, it has been found that anesthetic gas can permeate through the cuff and cause overinflation which can cause tracheal necrosis and/or stenosis. Therefore, there have been many efforts in the art to devise an indicator that detects proper inflation of the cuff.

For instance, a typical indicator used to indicate proper inflation of the cuff is a molded balloon. The balloon is attached to the end of the inflation channel that leads to the inflatable cuff. Inflation of the molded balloon directly correlates to the inflation of the cuff within the patient's trachea. Therefore, the balloon is designed to detect and indicate any changes in cuff pressure by visual inspection, or by pressing the balloon to "feel" the air pressure. However, the balloon is generally not sensitive enough to detect small pressure changes.

U.S. Pat. No. 4,361,107 to Gereg discloses a pressure indicating device for use with an endotracheal cuff. The device is added to a normal pilot balloon to indicate that a preset pressure has been exceeded. The device is folded inside itself when a low pressure is present, and becomes unfolded and elongated when a preset pressure has been exceeded. However, these indicators are often unreliable and prone to breakage.

U.S. Pat. No. 4,134,407 to Elam discloses a monitoring system for detecting the pressure and volume of an endotracheal cuff. The monitoring system is comprised of an elastomer balloon housed in a rigid cage having a plurality of windows which is designed to continuously indicate the state of collapse or expansion of the cuff of an endotracheal tube. The balloon monitor is connected in series with the pneumatic channel through which the cuff is inflated. The volume of the balloon may be observed visually with reference to its state of inflation, thereby visually indicating the level of inflation of the cuff. In addition, electrical means may be arranged between the balloon and the inner surface of the cage to produce a warning signal in the event of cuff overdistension and an alarm signal in the event of cuff collapse.

However, there are various disadvantages associated with this type of indicator. First, the visual indication of overinflation is detected by an inflation of a cavity of the balloon. There are various degrees to which the balloon may overinflate, and often times, it is left to the subjective determination of the health care professional to determine whether there is a potential overinflation. Therefore, this device lacks a simple, reliable, and objective indication for determining a dangerous overinflation of the cuff. While overinflation of the cuff may be determined by installing electrical means within the balloon, this is extremely costly.

U.S. Pat. No. 4,178,939 to Stephens discloses an apparatus for visually indicating the degree of inflation of an inflatable cuff which is adapted to be inserted into a body passageway. The apparatus comprises a hollow-walled tubular member formed with a plurality of ridges and valleys and is selectively inflatable into a balloon-like shape in response to the pressure of air applied to the cuff. The level of inflation of the cuff is subjectively determined by visual inspection of the inflatable balloon. Thus, this apparatus has similar disadvantages as it does not provide an objective and definitive determination of whether there is a dangerous overinflation of the cuff, but only indicates that an overinflated condition is present.

U.S. Pat. No. 4,856,510 to Kowaleski discloses a tracheal tube including an indicator assembly. The indicator assembly includes a pilot balloon and control balloon serially arranged to an inflation cuff, with the control balloon having a higher compliance than the pilot balloon and being connected directly to the inflation tube. The control balloon, because of its higher compliance, expands readily with very little increase in internal pressure. The result is that the pressure within the control balloon and the tracheal cuff remain fairly constant regardless of the amount of air introduced into the pilot balloon. However, the indicator assembly does improve the ease at which an overinflation may be detected. In addition, this indicator assembly is relatively complex in design, requiring multiple parts.

U.S. Pat. No. 4,617,015 to Foltz discloses a visual pressure indicator for endotracheal cuffs. The indicator comprises an indicating diaphragm which is sealingly positioned within a body by means of a cap. A hole is positioned within the cap to allow protrusion of an indicating stem of the diaphragm. The air space between the diaphragm and the body is connected in fluid communication with the cuff supply tube by means of passageways. The indicating diaphragm of the indicator flexes as the pressure within the cuff increases. As this pressure increases, the indicating stem of the diaphragm increasingly protrudes from the hole in the cap affixed to the body of the indicator. This indicating system has disadvantages, as there is no definitive and objective indication for determining when a dangerous overinflation has been reached. In addition, it is relatively complex in design, which is relatively expensive to manufacture.

Other types of indicator systems include the use of external pressure gauges, which measure the cuff pressure. An example of an external pressure gauge is manufactured by Rusch, Inc., in Duluth, Ga. However, these gauges are often extremely costly.

BRIEF SUMMARY OF THE INVENTION

In one aspect, the present invention provides an indicator for visually indicating a pressure level of a fluid in a pressure source. The indicator comprises an inflatable body having a notched section with opposing edge portions that are separated by a gap when the inflatable body is in an uninflated condition. The inflatable body further includes a port for connecting the inflatable body to the pressure source whereby upon inflation of the inflatable body, there is relative movement of the opposing edge portions in a direction so as to decrease the size of the gap and thereby indicate that a predetermined pressure has been reached.

In a further aspect, the present invention provides a surgical tube with an inflatable cuff having a visual indicator. The inflatable cuff is disposed on the surgical tube and includes an inflation conduit leading from the cuff. The visual indicator is attached in series with the inflation conduit and includes an inflatable body having a notched section separated by a gap with opposing edge portions. The inflatable body further includes a port for connecting the inflatable body to the inflatable cuff whereby upon inflation of the inflatable body, there is relative movement of the opposing edge portions in a direction so as to decrease the size of the gap and thereby indicate that a predetermined pressure has been reached in the cuff.

DETAILED DESCRIPTION OF THE INVENTION

Figure 1:
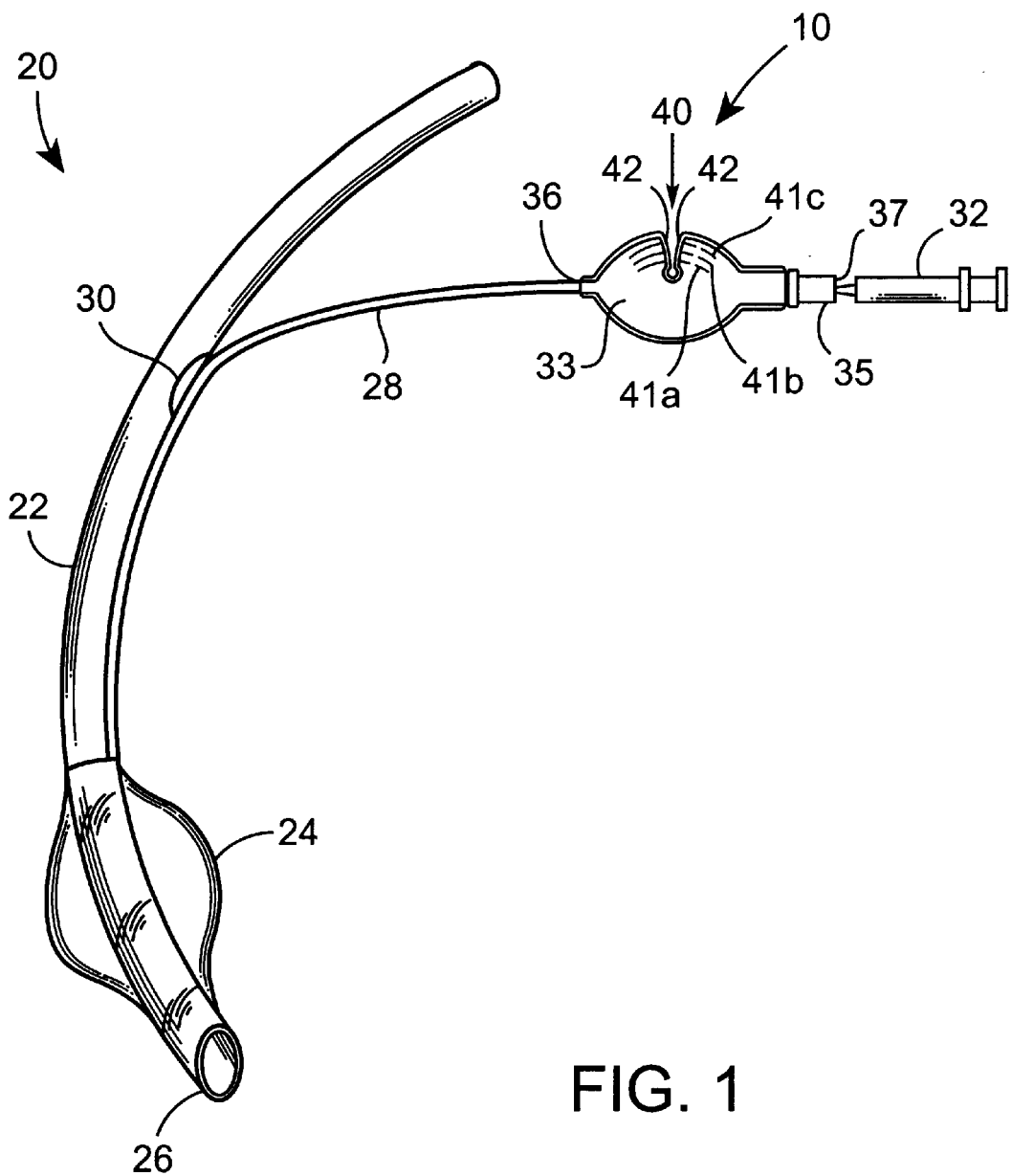
FIG. 1 is a perspective view of the visual indicator of the present invention as used in connection with a surgical tube.

As noted above, one aspect of the present invention relates to a visual indicator for indicating whether a predetermined pressure has been reached in a pressure source. With reference to FIG. 1, the visual indicator 10 is illustrated as it is used in connection with a surgical tube assembly 20. The surgical tube assembly 20 includes a surgical tube 22 having an inflatable cuff 24 conventionally constructed from polyvinyl chloride ("PVC"), polyurethane, or another elastomeric material near its distal end 26. Preferably, the surgical tube 22 is an endotracheal tube, with is intended for insertion into a patient's trachea. The endotracheal tube is flexible in nature and is preferably made from plastic, such as PVC, urethane, silicone or other elastomeric material, as well known in the art. However, while the visual indicator of the present invention will be described as it is used in conjunction with a surgical tube, and more specifically an endotracheal tube, it should be understood that it may be used with other medical equipment having pressure sources, such as medication delivery systems and the like.

The inflatable cuff 24 is connected to an inflation conduit 28, which is disposed partly within the wall of the surgical tube 22 and partly outside of the surgical tube 22 through an aperture 30. The inflation conduit 28 leads to the visual indicator 10, which leads to an inflation assembly 32. In the preferred embodiment, the inflation assembly 32 is an inflating syringe, that is used to inject air through the visual indicator 10 into the inflation conduit 28 and thereby inflate the inflatable cuff 24. However, it should be understood that other inflations assemblies may be used to inflate the inflatable cuff, such as a cuff inflation device or Endotest, which is a product manufactured by the Rusch, Inc., in Duluth Ga., as is well known in the art.

Preferably, the visual indicator 10 is arranged in series between the inflatable cuff 24 and the inflation assembly 32 and is in fluid communication with the inflatable cuff 24 by way of inflation conduit 28, which is preferably a small diameter tube composed of a conventional plastic material such as PVC. The inflation assembly 32 is in fluid communication with the visual indicator 10 by way a valve 35. The visual indicator 10 includes an inflatable body or balloon 33 having a port 36 which is in fluid communication with the inflatable cuff 24, and a port 37 which is connected to valve 35.

Alternatively, the visual indicator 10 may be connected only to the inflatable cuff 24, and is not disposed between the inflation assembly 32 and the inflatable cuff 24. In this alternative embodiment, the inflation assembly is connected to the inflatable cuff 24 by a separate inflation conduit, in a Y-shaped configuration, as is conventional in the art.

Preferably, the inflatable body 33 is elliptical in shape, but may be any shape, including but not limited to a rectangle, triangle, circle, hexagon, and octagon. It should also be understood that the shape need not be geometric, but may be any other shape. Preferably, the inflatable body 33 is made from PVC. Other materials may be used, such as polyethylene, urethane, polypropylene or other elastomeric. However, it should be understood that a variety of materials may be used, and may include any elastomeric material.

The inflatable body 33 includes a notched section 40 with opposing edge portions 42 which are separated by a gap. The term notch is used herein to describe any configuration with opposing edge portions 42 that may be moved towards each other upon inflation of the body 33, including a V-shape, a U-shape, concave shape, and the like. Therefore, the notched section 40 may be U-shaped, V-shaped, concave, or any other configuration that permits relative movement of the opposing edge portions 42 towards each other upon inflation of the body 33. However, when the pressure within the inflatable cuff 24 starts to increase, the gap between the opposing edge portions 42 decreases in size to indicate that a predetermined pressure has been reached, and more specifically, exceeded.

For the cuff of a typical endotracheal tube, the indicator 10 is constructed so that a pressure of 20–24 cm of water or below is indicated when the inflatable balloon 33 is slightly inflated. Preferably, the inflatable body 33 includes three bands 41a, 41b, and 41c, indicating the safe to danger zones for the cuff 24 pressure. Preferably, the bands are three different colors. More preferably, band 41a is green indicating a safe pressure, band 41b is yellow indicating a warning pressure, and band 41c is red indicating a danger level. The indicator 10 is so designed that as the green lines or band touches, the pressure in the cuff 24 is approximately 20–30 cm of water which is considered to be a safe pressure. However, when the gap between the opposing edge portions 42 starts to close so that bands 41b or 41c touch, this indicates that the cuff 24 has overinflated beyond the safe level of 30 cm. When this occurs, an attendant can reduce the pressure via the inflation assembly such as by slightly withdrawing the plunger from the syringe. It should be understood that the indicator 10 may be calibrated to indicate other predetermined pressure levels, depending on preference and application.

In addition, the behavior shape and size of the notched section 40 is largely dependent upon the type and thickness of material used for the inflatable body 33. The angle of the opposing edge portions 42 in its uninflated condition is dependent on the pressures one is trying to simulate.

Therefore, the notched section 40 may be constructed to have different angles depending on the application for the inflatable body 33. For instance, the stronger the material, which can be obtained with thicker material, the smaller the angle of the notched section 40. Stronger material can be used, for instance, where higher pressures are to be indicated such as for tires, other inflation devices, and fluid in conduits.

Preferably, the indicator body 33 is manufactured by sealing two pieces of PVC or elastomeric material between a pair of dies, as is commonly known in the art. The dies are manufactured in the desired shape. The inlet and outlet portion of the inflation conduit 28 are placed onto the die, so that the inflation conduit becomes properly attached to the inflation body 33. The two pieces of material, and inlet and outlet portion, are sealed by heat, radio frequency, or any other sealing technique known in the art. As a possible alternative, the indicator body can be prepared by a blow molding process or any other technique that can provide the desired structure. Each end of the indicator, namely the tube 28 and the valve 35 can be solvent bonded after the sealing process.

Figure 2:
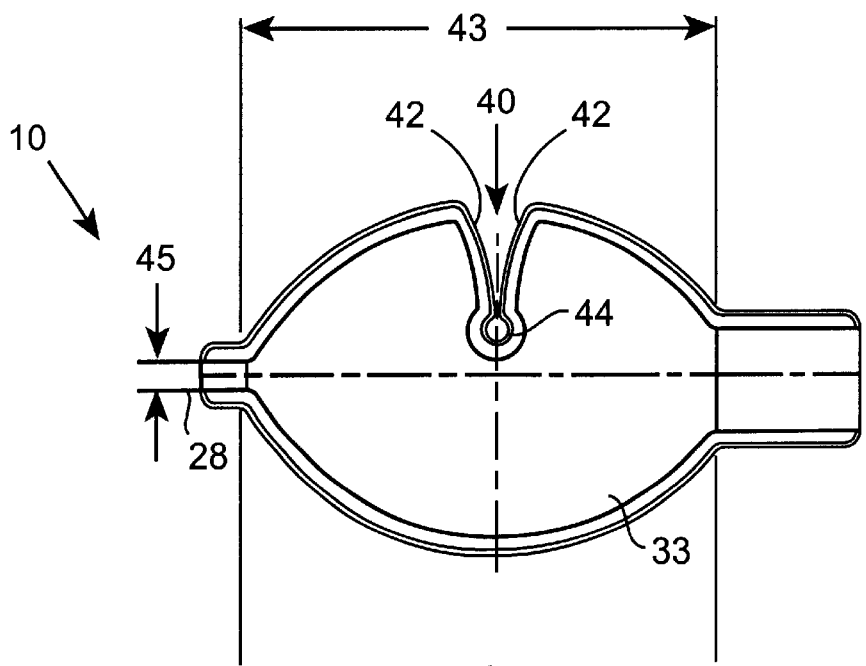
FIG. 2 is a side elevational view of a preferred embodiment of the visual indicator of the present invention.

With reference now to FIG. 2, the specific configuration and dimensions of the preferred embodiment of the indicator 10 and the notched section 40 in its normal, uninflated condition, will be described in more detail. Preferably, the indicator 10 is made from PVC, urethane, polyethylene, polypropylene or other elastomeric material. The notched section 40 of the indicator 10 includes a tear drop shaped portion 44, with two opposing edge portions 42. The inflatable body 33 is preferably elliptical in shape with a major axis 43 measuring approximately 1.30 inches. The outside diameter 45 of the inflation conduit 28 is approximately 0.080 inches.

Figure 3:
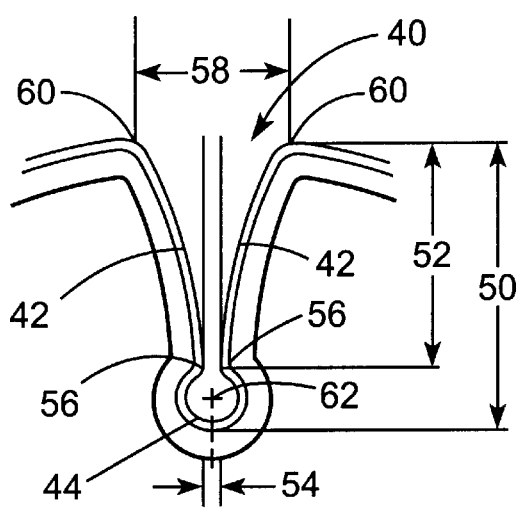
FIG. 3 is an enlarged, cut away side elevational view of the notched section of the indicator of FIG. 2.

With reference now to FIG. 3, the preferred dimensions of the notched set 40 will be further described. It should be understood that the following description of the preferred dimensions is exemplary, and is not intended to limit the scope of the invention. The opposing edges 42 have an equal radius of approximately 0.838 inches, while the tear drop portion 44 has a radius of approximately 0.030 inches. The vertical height 50 is approximately 0.365 inches, while the height 52 after the tear drop is approximately 0.290 inches. The distance 54 between points 56 is approximately 0.020 inches and the distance 58 between points 60 along the top opening of the notch 40 is approximately 0.181 inches. However, it should be understood that other radii are possible as well as various openings, depending on the type of material used and application.

The notched section 40 is designed so that when there is no pressure in the inflatable cuff 24 of FIG. 1, the notched section 40 is configured as illustrated with respect to FIG. 3 in its uninflated condition. However, if the pressure in the inflatable cuff 24 increases, the opposing edge portions 42 move towards each other. Specifically, the notched section 40 may be constructed and calibrated so that when the first 0.100 inches of the opposing edges touch, the safe pressure of between about 20 cm of water and 30 cm of water, and most preferably about 24 cm of water, is attained. A green band 41a or other marking is used to indicate to a user that the pressure is safe, as shown in FIG. 1.

The notched section 40 is also calibrated and configured so that when the next 0.100 inches of the opposing edges 42 touch, the pressure in the inflatable cuff 24 has increased to the warning pressure. Warning pressure ranges preferably from about 30 cm of water and 50 cm of water. An amber band 41b or other marking is used to indicate to a user that the pressure in the inflatable cuff 24 has increased to a warning level, as shown in FIG. 1.

The notched section 40 is also calibrated and configured so that when distal ends 60 are adjacent, a danger level of pressure or overinflation is indicated. Preferably, the dangerous pressure range is between about 50 cm of water and 80 cm of water, and most preferably about 80 cm of water. A red band 41c or other marking is used to indicate to a user that the pressure in the inflatable cuff 24 has increased to a dangerous level, as shown in FIG. 1.

Figure 4:
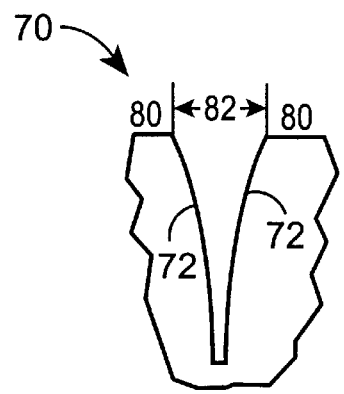
FIG. 4 is an enlarged, cut away side elevational view of a first alternative embodiment of the notched section of the indicator of the present invention.

With reference now to FIG. 4, a first alternative configuration of the notched section 70 in its uninflated condition is illustrated. The notched section 70 is substantially V-shaped, with two opposing edge portions 72 curving slightly outwardly. The distal ends 80 of the opposing edge portions 72 are separated by a width 82.

Various markings may be positioned along the opposing edge portions 72 to indicate pressures over the predetermined pressure. For instance, a red marking may be positioned at the distal ends 80, so that when the distal ends 80 are substantially adjacent and the width 82 is close to zero, this would indicate that the pressure in the inflatable cuff 24 has gone beyond the predetermined pressure.

Figure 5:
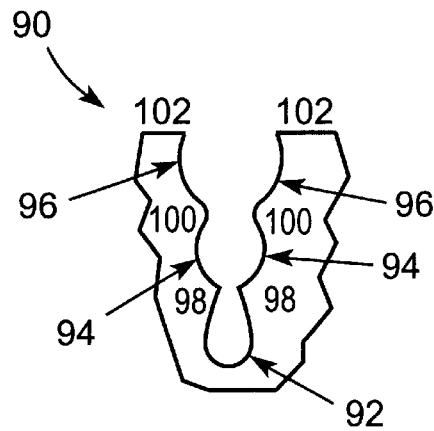
FIG. 5 is an enlarged, cut away side elevational view of a second alternative embodiment of the notched section of the indicator of the present invention.

With reference now to FIG. 5, a second alternative configuration of the notched section 90 will be described. The notched section 90 includes a curved-base portion 92, curved intermediate portions 94, and curved distal end portions 96. Preferably, the curved intermediate portions 94 and the curved distal end portions 96 are concave. Various markings may be positioned along notched section 90, in a manner similar to that described with respect to the preferred embodiment. Most preferably, markings may be placed at the intersections 98 of the intermediate portions 94 with the base portion 92, the intersections 100 of the intermediate portions 94 with the distal end portions 96, and the distal ends 102 of the distal end portions 96, to thereby indicate safe, warning, and/or dangerous inflation levels, when the respective intersections are connected.

Thus, the present invention provides a simple visual indication of pressure in a pressure source. This is particularly useful for determining whether there is an overinflated condition within a inflatable cuff 24, without the use of expensive gauges or devices, which is both accurate and simple to use and manufacture.

Although the present invention has been described with reference to certain preferred embodiments, it is apparent that modifications and variations thereof may be made by those skilled in the art without departing from the scope of the invention as defined the following claims.

What is claimed is:

1. An indicator for visually indicating a pressure level of a fluid in a pressure source, said indicator comprising an inflatable body having a notched section with opposing edge portions that are separated by a gap when the inflatable body is in an uninflated condition, said inflatable body further having a port for connecting the inflatable body to the pressure source whereby upon inflation of the inflatable body, there is relative movement of the opposing edge portions in a direction so as to decrease the size of the gap and thereby indicate that a predetermined pressure has been reached in the pressure source.

2. The indicator of claim 1, wherein the notched section is tear drop and V-shaped.

3. The indicator of claim 1, wherein the notched section is substantially concave.

4. The indicator of claim 1, wherein the inflatable body is elliptical in shape.

5. The indicator of claim 1, wherein said inflatable body is round in shape.

6. The indicator of claim 1, wherein said notched section includes a base portion wherein said opposing edge portions extend from said base portion, said base portion being substantially circular in shape, and the opposing edge portions extending in a tear drop shaped configuration.

7. The indicator of claim 1, wherein said notched section includes a curved base portion, curved intermediate portions extending from said base portion, and distal end portions extending from said intermediate portions, wherein said intermediate portions and said distal end portions are concave.

8. The indicator of claim 1, wherein at least one set of markings are disposed along opposing edge portions to indicate the pressure in the pressure source is beyond the predetermined pressure when the markings are connected.

9. The indicator of claim 1, wherein said at least one set of markings include the use of colors to indicate that various predetermined pressures have been reached.

10. The indicator of claim 1, wherein said inflatable body is made polyvinyl chloride, urethane, polypropylene, or polyethylene.

11. A surgical tube assembly, comprising:

a surgical tube;

an inflatable cuff disposed on said surgical tube;

an inflation conduit leading from said inflatable cuff; and an indicator attached in series with the inflation conduit, said indicator including an inflatable body having a notched section separated by a gap with opposing edge portions, said inflatable body further having a port for connecting the inflatable body to said cuff whereby upon inflation of the inflatable body, there is relative movement of the opposing edge portions in a direction so as to decrease the size of the gap and thereby indicate that a predetermined pressure has been reached in said cuff.

12. The surgical tube of claim 11, wherein said surgical tube is an endotracheal tube and said pressure source is an endotracheal cuff.

13. The indicator of claim 11, wherein the notched section is tear drop and V-shaped.

14. The indicator of claim 11, wherein the notched section is substantially concave.

15. The indicator of claim 11, wherein the inflatable body is elliptical in shape.

16. The indicator of claim 11, wherein said inflatable body is round in shape.

17. The indicator of claim 11, wherein said notched section includes a base portion wherein said opposing edge portions extend from said base portion, said base portion being substantially circular in shape, and the opposing edge portions extending in a substantially V-shaped configuration.

18. The indicator of claim 11, wherein said notched section includes a curved base portion, curved intermediate portions extending from said base portion, and distal end portions extending from said intermediate portions, wherein said intermediate portions and said distal end portions are concave.

19. The indicator of claim 11, wherein at least one set of markings are disposed along opposing edge portions to indicate the pressure in the pressure source is beyond the predetermined pressure when the markings are connected.

20. The indicator of claim 19, wherein said at least one set of markings include the use of colors to indicate that various predetermined pressures have been reached.

21. The indicator of claim 11, wherein said inflatable body is made from polyvinyl chloride, urethane, polypropylene, or polyethylene.

* * * * *